United States Patent [19]

Nishikawa et al.

[11] 4,388,243

[45] Jun. 14, 1983

[54] PROCESS FOR THE PREPARATION OF ACTIVE-TYPE VITAMIN $D_3$ COMPOUNDS

[75] Inventors: Osamu Nishikawa; Kenji Ishimaru, both of Iwakuni; Toru Takeshita, Hino; Hideki Tsuruta, Iwakuni, all of Japan

[73] Assignee: Teijin Limited, Osaka, Japan

[21] Appl. No.: 371,870

[22] Filed: Apr. 26, 1982

Related U.S. Application Data

[63] Continuation of Ser. No. 199,126, Oct. 22, 1980.

[30] Foreign Application Priority Data

Oct. 23, 1979 [JP] Japan .............................. 54-135871
Dec. 27, 1979 [JP] Japan .............................. 54-169464
Dec. 27, 1979 [JP] Japan .............................. 54-169465
Apr. 18, 1980 [JP] Japan .............................. 55-50258

[51] Int. Cl.$^3$ ............................................. C07J 9/00
[52] U.S. Cl. .............................................. 260/397.2
[58] Field of Search ................................... 260/397.2

[56] References Cited

U.S. PATENT DOCUMENTS 3,993,675 11/1976 Uskokovic et al. ............... 260/397.2
4,011,250 3/1977 Iskikawa et al. .................. 260/397.2
4,226,788 10/1980 De Luca et al. ................... 260/397.2

*Primary Examiner*—Elbert L. Roberts
*Attorney, Agent, or Firm*—Sughrue, Mion, Zinn, Macpeak and Seas

[57] ABSTRACT

The present invention relates to a novel process for the preparation of active-type vitamin $D_3$ compounds and their intermediates. In accordance with the present invention, a large amount of an active-type vitamin $D_3$ compounds, for example 1α-hydroxycholecalciferol, 1α,25-dihydroxycholecalciferol and the like, is efficiently prepared with high industrial advantages by a novel processes, which comprises (i) reacting hydroxycholesta-5-enes having the hydroxyl groups protected with lower alkoxycarbonyl group as a starting material with allylic brominating agent and dehydrobrominating agent to prepare the corresponding hydroxycholesta-5,7-dienes, (ii) exposing the hydroxycholesta-5,7-dienes to ultraviolet irradiation or to a combination of the irradiation with thermal isomerization to obtain a mixture of the unreacted hydroxycholesta-5,7-dienes and previtamin $D_3$ compounds or a mixture of the unreacted hydroxycholesta-5,7-dienes and the protected active-type vitamin $D_3$ compounds, (iii) separating the mixture into the unreacted hydroxycholesta-5,7-dienes and previtamin $D_3$ compounds or the protected active-type vitamin $D_3$ compounds, (iv) recycling the unreacted hydroxycholesta-5,7-dienes as reuse and (v) thermally isomerizing the remaining compounds and/or splitting off the protective groups. The process for the preparation of active-type vitamin $D_3$ compounds, in the present invention, is of very high industrial value, capable of carrying out by simple operation and adaptable to large scale commercial production.

14 Claims, No Drawings

PROCESS FOR THE PREPARATION OF ACTIVE-TYPE VITAMIN D3 COMPOUNDS

This is a continuation of application Ser. No. 199,126, filed Oct. 22, 1980.

The present invention relates to a novel process for the preparation of active-type vitamin D3 compounds and their intermediates. More particularly, the present invention relates to a novel process for the preparation of active-type vitamin D3 compounds including 1α-hydroxycholecalciferol, 1α,24-dihydroxycholecalciferol, 1α,25-dihydroxycholecalciferol and the like, which are used for controlling the calcium metabolism in warm-blooded animals, and their intermediates in high yield, thus being of highly industrial value.

Up to now, active-type vitamin D3 compounds, for example, 1α-hydroxycholecalciferol or the like, have been prepared, for example, as described in Japanese patent laid open No. 48-62570 or Tetrahedron Letters 40 4147–4150 (1972), by starting from a hydroxycholest-5-ene having hydroxyl groups protected with acetyl groups, for example, 1α,3β-diacetoxycholest-5-ene, 1α,3β,24-triacetoxycholest-5-ene or the like, the allylic bromination and subsequent dehydrobromination to form the corresponding hydroxycholesta-5,7-diene, the irradiation of the product with ultraviolet rays, the thermal isomerization, and the elimination of the protecting groups.

Further, Chem, Pharm, Bull, 23 685–697 (1975) and others describe another method of the preparation of active-type vitamin D3 compounds that starts from a hydroxycholest-5-ene protected with benzoyl groups and comprises the steps of allylic bromination and dehydrobromination to form the corresponding hydroxycholesta-5,7-diene, the irradiation of the product with ultraviolet rays and the thermal isomerization.

However, in these processes, the allylic bromination of a hydroxycholest-5-ene followed by dehydrobromination gives the corresponding hydroxycholesta-5,7-diene in an isolation yield as low as 15 to 30% and the yield reproducibility is low. Further, since the relatively high proportion of a hydroxycholesta-4,6-diene formed as a by-product in the reaction mixture causes difficulty to isolate the requisite hydroxycholesta-5,7-diene, they can not be regarded as satisfactory processes for the preparation of active-type vitamin D3 compounds.

In the meantime, conventional steps of ultraviolet irradiation and thermal isomerization reaction as the final stage for the preparation of active-type vitamin D3 compounds give unsatisfactorily very low yield.

For example, according to an example in the specification of Japanese patent laid open No. 48-62750, the irradiation of 600 micrograms of 1α,3β-diacetoxycholesta-5,7-diene with ultraviolet rays forms only 120 micrograms of 1α,3β-diacetoxyprevitamin D3 and the specification of Japanese patent laid open No. 51-110554 describes that 135 milligrams of 1α,3β-diacetoxycholesta-5,7-diene is led to only 13 milligrams of 1α-hydroxycholecarciferol and 8 milligrams of 1α-hydroxyprevitamin D3.

Japanese patent laid open No. 51-108050 and 53-87344 describe another process for the preparation of active-type vitamin D3 compounds in which the irradiation of a hydroxycholesta-5,7-diene with ultraviolet rays is stopped when the conversion of the hydroxycholesta-5,7-diene reaches about 50% to prevent the corresponding previtamin D3 formed by the irradiation from further converting to other compounds, for example, corresponding tachysterol, lumisterol and others, the unreacted hydroxycholesta-5,7-diene is separated from the previtamin D3 and recycled to the irradiation step, and the previtamin D3 is thermally isomerized and eliminated the protecting groups.

However, in the above process, the separation of the previtamin D3 from the unreacted hydroxycholesta-5,7-diene after ultraviolet irradiation is effected by high-speed liquid chromatography, which has a possibility to decompose the previtamin D3 during the operation because of its instability. Further, high-speed liquid chromatography can not treat a large amount of compounds at a time and so is not always satisfactory as an industrial procedure for the preparation of active-type vitamin D3 compounds.

An object of the present invention is to provide an excellent process for the preparation of hydroxycholesta-5,7-diene series, the intermediates of active-type vitamin D3 compounds.

Another object of the present invention is to propose industrially excellent steps for the ultraviolet irradiation and thermal isomerization, the final stage for the preparation of active-type vitamin D3 compounds.

Further, another object of the present invention is to propose an industrially excellent sequence of steps for the preparation of active-type vitamin D3 compounds.

Other objects of the present invention will become apparent from the description which follows.

The objects and advantages of the present invention mentioned above can be accomplished by adopting a new synthetic path way described below.

Namely, the new synthetic path way is for the preparation of hydroxycholesta-5,7-dienes of the following formula [II]

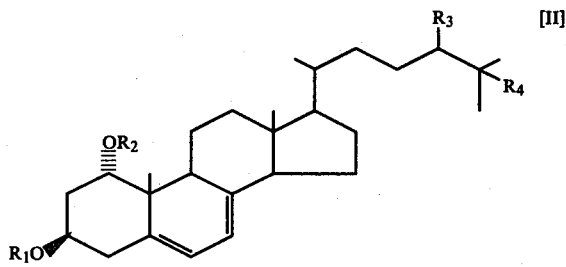

wherein $R_1$ and $R_2$ represent a lower alkoxycarbonyl group, $R_3$ represents a hydrogen atom or a lower alkoxycarbonyloxy group and $R_4$ represents a hydrogen atom, a lower alkoxycarbonyloxy group or a hydroxyl group, which comprises reacting hydroxycholest-5-enes of the following formula [II]

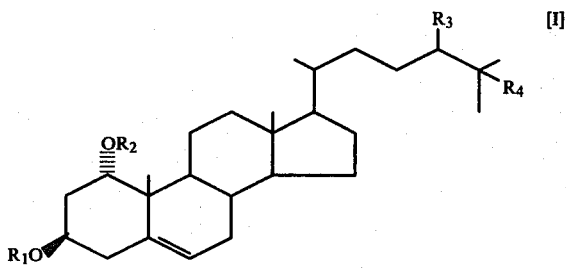

wherein $R_1$, $R_2$, $R_3$ and $R_4$ are the same as defined above, with an allylic brominating agent in an inert organic solvent, and then contacting the resulting reaction mixture with a dehydrobrominating agent.

In the process of the present invention, a hydroxycholest-5-ene having hydroxyl groups protected with lower alkoxycarbonyl groups is used as a starting material and the employment of such a compound enables the efficient formation of hydroxycholesta-5,7-dienes in high yield by restraining the transformation to hydroxy-4,6-dienes, a byproduct. Further, the resulting hydroxycholesta-5,7-dienes protected with lower alkoxycarbonyl groups permits the high efficient ultraviolet irradiation and thermal isomerization, which are the final stage for the preparation of active-type vitamin $D_3$ compounds. The hydroxycholest-5-enes and hydroxycholesta-5,7-dienes mentioned above have not been described in literatures, being novel compounds that have been synthesized by the present inventors for the first time.

In aforesaid formula [I], $R_1$ and $R_2$ are lower alkoxycarbonyl groups, $R_3$ is hydrogen atom or lower alkoxycarbonyloxy group and $R_4$ is hydrogen atom, lower alkoxycarbonyloxy or hydroxyl group. Suitable lower alkoxycarbonyl groups in the present invention include methoxycarbonyl, ethoxycarbonyl, propoxycarbonyl, butoxycarbonyl, and so forth and methoxycarbonyl or ethoxycarbonyl group is most preferred. As $R_4$ is a tertiary substituent and undergoes steric hindrance, the reactivity is low and it exerts little effects on the reaction course of the preparation of hydroxycholesta-5,7-dienes. Consequently in the present invention $R_4$ includes free hydroxyl group too.

Concrete examples of cholest-5-enes of formula (I) are given as follows:

(1) 1α,3β-diethoxycarbonyloxycholest-5-ene,
(2) 1α,3β-dimethoxycarbonyloxycholest-5-ene,
(3) 1α,3β,24-triethoxycarbonyloxycholest-5-ene,
(4) 1α,3β,24-trimethoxycarbonyloxycholest-5-ene,
(5) 1α,3β,25-triethoxycarbonyloxycholest-5-ene,
(6) 1α,3β,25-trimethoxycarbonyloxycholest-5-ene,
(7) 1α,3β,24,25-tetraethoxycarbonyloxycholest-5-ene,
(8) 1α,3β,24,25-tetramethoxycarbonyloxycholest-5-ene,
(9) 1α,3β-diethoxycarbonyloxy-25-hydroxycholest-5-ene, and
(10) 1α,3β-dimethoxycarbonyloxy-25-hydroxycholest-5-ene.

Said hydroxycholest-5-enes of formula (I) are readily prepared by, for example, reaction between hydroxycholest-5-enes having free hydroxyl groups and ethyl chloroformate in the presence of a catalyst of tertiary amine, for example, 4-dimethylaminopyridine. The reaction proceeds at room temperature to 80° C. Since ethyl chloroformate boils at a low temperature, some caution is required during the reaction and the desirable reaction time is usually 20 to 30 hours.

The resulting hydroxycholest-5-enes having hydroxyl groups protected with lower alkoxycarbonyl group are subjected to reactions with an allylic brominating agent and subsequently with a dehydrobrominating agent to give requisite hydroxycholesta-5,7-dienes, intermediates of active-type vitamin $D_3$ compounds.

In the present invention any usual allylic brominating agent may be employed and suitable brominating agents include N-bromosuccimide, 1,3-dibromo-5,5-dimethylhydantoin, N-bromocaprolactam and the like. The amount of these allylic brominating agent used is usually 1 to 2 times the molar quantity of the starting hydroxycholest-5-enes of formula (I).

The allylic bromination in the present invention is effected by making an allylic brominating agent act on a hydroxycholest-5-ene of formula (I) in an inert organic solvent wherein the suitable temperature is room temperature to 140° C.

The inert organic solvent is required to be unreactive with the allylic brominating agent. Suitable inert organic solvents include hydrocarbons and halogenated hydrocarbons such as hexane, heptane, cyclohexane, ligroin, benzene, toluene, xylene, bromobenzene, chlorobenzene, nitrobenzene, carbon tetrachloride 1,2-dichloroethane, or 1,2-dibromoethane.

Further, ethereal solvents, for example, ethyl ether, tetrahydrofuran, dioxane, methylcellosolve or phenylcellosolve, are also employed.

These inert organic solvents may be used alone or in form of mixture.

The reaction proceeds at aforementioned temperatures, however, active rays of wave length in the region from infrared to ultraviolet may be irradiated in the brominating reaction. In such a case, the reaction proceeds even at a lower temperature than room one. Further, a small amount of radical initiator such as azobisisobutyronitrile, benzoyl peroxide or cyclohexenyl hydroperoxide may be added.

The brominated hydroxycholest-5-enes resulting from the above reaction is made to contact with a dehydrobrominating agent and transformed to corresponding hydroxycholesta-5,7-dienes of formula (II).

In this reaction, the reaction solvent is not always necessary, because some dehydrobrominating agents can serve as a reaction solvent as they are. In cases where reaction solvents are employed, as a solvent suitable for the dehydrobromination is not always the same as that suitable for the preceding bromination, the dehydrobromination is usually effected in a newly added solvent after removal of the solvent employed in the preceding reaction.

Suitable reaction solvents include xylene, bromobenzene, chlorobenzene, hexamethylphosphoramide, dimethylformamide, dimethylacetamide, and so forth.

Suitable dehydrobrominating agents includes trimethyl phosphite, S-collidine, diethylaniline and the like and they may be combined. Theoretically, the equimolar amount of an agent is sufficient to cause the reaction, however, desirable reaction rate and yield are attained when about two or more moles are used for each mole of said brominated compound. As described above, some dehydrobrominating agents serve also as a reaction solvent and there is no specified upper limit in the amount employed.

The reaction usually proceeds at a temperature of from 100° to 180° C. suitably. The reaction time depends upon the dehydrobrominating agent and reaction solvent, however, in an preferable example where the reaction is effected in xylene-S-collidine system under reflux, the reaction reaches completion in a short time of about 20 minutes.

After completion of the reaction, the reaction product, corresponding hydroxycholesta-5,7-dienes, is separated and purified by removing the solvent from the reaction mixture and recrystallizing the residue.

The preparation of hydroxycholesta-5,7-dienes starting from hydroxycholest-5-enes having hydroxyl groups protected with lower alkoxycarbonyl groups in accordance with the present invention results in higher yield as compared with to conventional processes and reduces the proportion of hydroxycholesta-4,6-dienes formed as a by-product. Additionally, the protecting group of lower alkoxycarbonyl increases the crystallizability of the requisite compound. These merit of this invention provides a great advantage that the isolation and purification of hydroxycholesta-5,7-dienes resulting from the aforementioned allylic bromination and dehydrobromination can be readily effected by a simple method of recrystallization.

The recrystallization is conducted preferably by a conventional method using a mixed solvent consisting of lower aliphatic alcohol such as methanol, ethanol, n-propanol, isopropanol, n-butanol, methoxyethanol, n-hexanol or the like and lower aliphatic ether such a dimethyl ether, diethyl ether, di-isopropyl ether, tetrahydofuran, dioxane, 1,2-dimethoxyethane or the like.

In this manner mentioned above, are prepared hydroxycholesta-5,7-dienes including 1α,3β-diethoxycarbonyloxycholesta-5,7-diene, 1α,3β-dimethoxycarbonyloxycholesta-5,7-diene, 1α,3β,24-triethoxycarbonyloxycholesta-5,7-diene, 1α,3β,24-trimethoxycarbonyloxycholesta-5,7-diene, 1α,3β,25-triethoxycarbonyloxycholesta-5,7-diene, 1α,3β,25-trimethoxycarbonyloxycholesta-5,7-diene, 1α,3β-diethoxycarbonyloxy-25-hydroxycholesta-5,7-diene and so forth in high efficiency. The resulting hydroxycholesta-5,7-dienes are subjected to the ultraviolet irradiation and thermal isomerization reaction, which are the final stage for the preparation of active-type vitamin $D_3$ compounds.

The present invention involves two kinds of ways as the final stage as follows:

(A). A process for preparing active-type vitamin $D_3$ compounds of the following formula [IV]

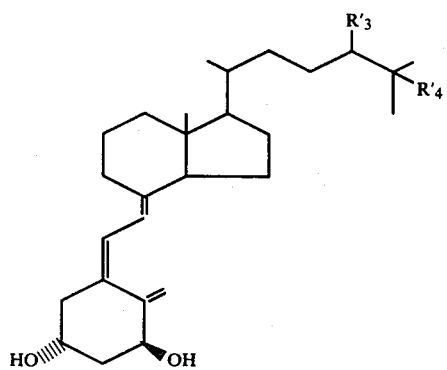

wherein $R_3'$ and $R_4'$ independently represents a hydrogen atom or a hydroxyl group, which comprises:

(i) exposing hydroxycholesta-5,7-dienes of the following formula [II]

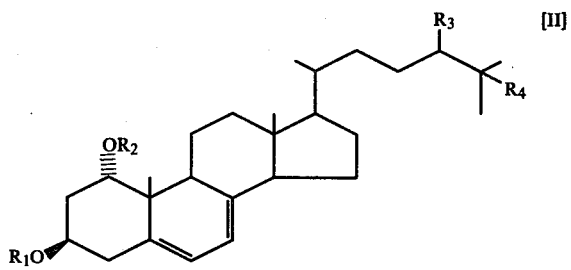

wherein $R_1$ and $R_2$ represent a lower alkoxycarbonyl group, $R_3$ represents a hydrogen atom or a lower alkoxycarbonyloxy group and $R_4$ represents a hydrogen atom, a lower alkoxycarbonyloxy group or a hydroxyl group, to ultraviolet irradiation in an inert organic solvent to obtain the mixture of previtamin $D_3$ compounds, of the following formula [III]

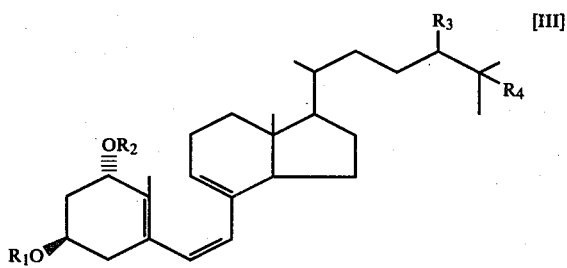

wherein $R_1$, $R_2$, $R_3$ and $R_4$ are the same as defined above, and the unchanged hydroxycholesta-5,7-dienes of the formula [II];

(ii) separating the mixture into the previtamin $D_3$ compounds and the unchanged hydroxycholesta-5,7-dienes;

(iii) recycling the unchanged hydroxycholesta-5,7-dienes through the ultraviolet irradiation; and (iv) thermally isomerizing the previtamin $D_3$ compounds and splitting off the protective groups.

(B) A process for preparing active-type vitamin $D_3$ compounds of the following formula [IV]

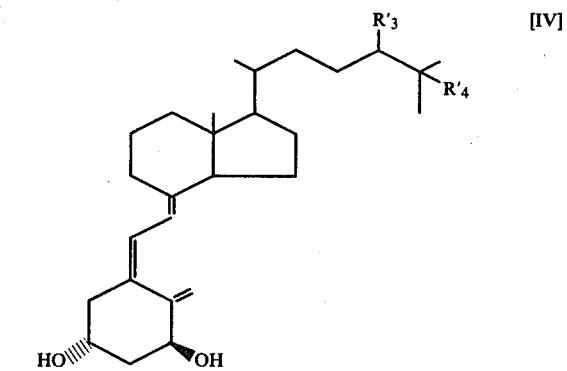

wherein $R_3'$ and $R_4'$ represent a hydrogen atom or a hydroxyl group, which comprises:

(i) exposing hydroxycholesta-5,7-dienes of the following formula [II]

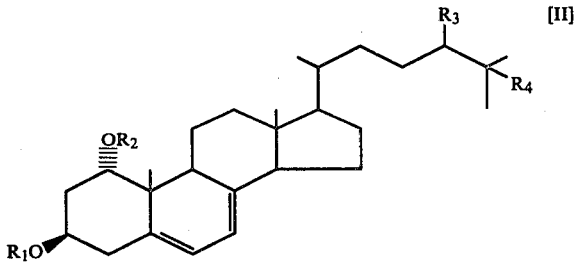

wherein $R_1$ and $R_2$ represent a lower alkoxycarbonyl group, $R_3$ represents a hydrogen atom or a lower alkoxycarbonyloxy group and $R_4$ represents a hydrogen atom, a lower alkoxycarbonyloxy group or a hydroxyl group, to ultraviolet irradiation in an inert organic solvent, then thermally isomerizing to obtain the mixture of protected active-type vitamin $D_3$ compounds of the following formula [V]

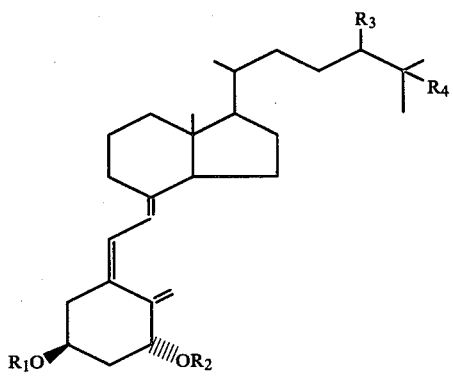

wherein $R_1$, $R_2$, $R_3$ and $R_4$ are the same as defined above, and the unchanged hydroxycholesta-5,7-dienes of the formula [II];

(ii) separating the mixture into the protected active-type vitamin $D_3$ compounds and the unchanged hydroxycholesta-5,7-dienes;

(iii) recycling the unchanged hydroxycholesta-5,7-dienes through the ultraviolet irradiation; and (iv) splitting off the protective groups of the protected active-type vitamin $D_3$ compounds According to method (A) or (B), the ultraviolet irradiation and thermal isomerization are effected in high efficiency and yield by simple operations, thus being adaptable to large scale commercial production.

Consequently, according to the present invention, are provided industrially excellent procedures for the ultraviolet irradiation and thermal isomerization, which are the final stage for the preparation of active-type vitamin $D_3$ compounds, and an industrially excellent sequence of steps for the preparation of active-type vitamin $D_3$ compounds starting from the hydroxycholesta-5-enes.

In the ultraviolet irradiation in accordance with methods (A) and (B), the ultraviolet rays employed range in wave length from about 200 to 360 millimicron, preferably from 260 to 310 millimicron.

As a reaction solvent, an inert organic solvent is preferred and suitable solvents include hydrocarbons and halogenated hydrocarbons such as hexane, heptane, cyclohexane, ligroin, benzene, toluene, xylene, bromobenzene, chlorobenzene, nitrobenzene, carbon tetrachloride 1,2-dichloroethane, 1,2-dibromoethane or the like, ethereal solvents such as diethyl ether, tetrahydrofuran, dioxane, methylcellosolve, phenylcellosolve or the like and alcoholic solvents such as methanol, ethanol, propanol, hexanol, cyclohexanol or the like. Especially benzene, toluene, diethyl ether, methanol and ethanol are preferred and they are used alone or in form of mixture.

The ultraviolet irradiation is effected at temperatures of from $-20°$ to $120°$ C. and the range from $-10°$ to $20°$ C. is especially preferred. Further, the irradiation is preferably effected under an oxygen-free inert atmosphere of argon or nitrogen gas.

In the methods A and B of the present invention, the ultraviolet irradiation is desirably stopped at a level of low conversion of hydroxycholesta-5,7-dienes and especially the ultraviolet irradiation is preferably stopped at a level of 0.1 to 50% conversion, much preferably 10 to 40%, and most preferably 10 to 30%. The discontinuation of ultraviolet irradiation at a low conversion supresses the further undesirable converting of the previtamin $D_3$ compounds of formula (III) formed by the irradiation to useless other compounds, for example, corresponding lumisterols and tachysterols, resulting in increase in the proportion of the previtamin $D_3$ compounds formed.

As a result, the ultraviolet irradiation gives a mixture of previtamin $D_3$ compounds and unreacted hydroxycholesta-5,7-dienes, from which, in method A, the products, previtamin $D_3$ compounds and the unreacted hydroxycholesta-5,7-dienes are isolated.

According to method A of the present invention, a hydroxycholesta-5,7-dienes protected with lower alkoxycarbonyl groups is employed as a starting material and converted by ultraviolet irradiation to a mixture of previtamin $D_3$ and unreacted hydroxycholesta-5,7-diene, both of which have hydroxyl groups protected with lower alkoxycarbonyl groups. The resulting mixture of previtamin $D_3$ compounds and unreacted hydroxycholesta-5,7-dienes is readily separated by simple recrystallization from or rinsing with an organic solvent, utilizing the difference in solubility between them, without aid of high-speed liquid chromatography. Thus, the process for the preparation of active-type vitamin $D_3$ compounds according to the present invention is capable of readily separating both compounds by simple procedures and provides a very large possibility of establishing an industrially high efficient method.

In the separation, after ultraviolet irradiation, a part of the reaction solvent is distilled off and the solid material or crystals formed is filtered by a usual method, whereby the reaction mixture is divided into crystals or the solid material of cholesta-5,7-dienes and filtrate containing previtamin $D_3$ compounds. Or after ultraviolet irradiation, the reaction solvent is distilled off and an alcoholic solvent such as methanol, ethanol, isopropanol, hexanol, cyclohexanol, or the like or a mixture thereof with an ethereal solvent such as diethyl ether, tetrahydrofuran, or the like is added to the residue to form solid materials or crystals, which are subjected to the same operations as mentioned above to separate the unreacted hydroxycholesta-5,7-dienes from the previtamin $D_3$ compounds.

The previtamin $D_3$ compounds formed by ultraviolet irradiation may be partially isomerized to the active-type vitamin $D_3$ compounds by heat energy, however, the active-type vitamin $D_3$ compounds formed is also separated together with the previtamin $D_3$ compounds in the above separation step.

The unreacted hydroxycholesta-5,7-dienes separated is recycled for reuse as a starting material and the previtamin $D_3$ compound is subjected to consequent thermal isomerization and splitting off the protective groups.

The thermal isomerization is preferably effected in an inert organic solvent and suitable solvents include the same ones as those which are used in the ultraviolet irradiation.

The thermal isomerization is an equilibrium reaction between a previtamin $D_3$ compound and the corresponding active-type vitamin $D_3$ compound. The equilibrium value varies with the reaction temperature and generally as the isomerization temperature rises higher, the isomerization reaction from previtamin $D_3$ to vitamin $D_3$ increases the rate, whereas the equilibrium value of vitamin $D_3$ shifts to the reduction side. In view of such situation, the isomerization reaction is effected at 20° to 120° C., preferably at 40° to 100° C.

The thermal isomerization reaction gives an active-type vitamin $D_3$ compounds protected with lower alkoxycarbonyl groups, which is subsequently isolated and purified or the thermal isomerization reaction, without isolation and purification, is followed by the splitting off the protective groups.

On the other hand, in the present invention, immediately after the ultraviolet irradiation, the resulting previtamin $D_3$ compounds may be subjected to the reaction of splitting off the protective groups followed by the thermal isomerization.

In method (B) of the present invention, the reaction mixture after ultraviolet irradiation, containing previtamin $D_3$ compound and unreacted hydroxycholesta-5,7-dienes, is directly subjected to thermal isomerization without separation from each other. The thermal isomerization is carried out under the same conditions as those in method A and suitable organic solvents include those which are preferably used in the ultraviolet irradiation in method A. The reaction temperature is 20° to 120° C., preferably 40° to 100° C.

In method (B), a mixture of active-type vitamin $D_3$ compound having protected hydroxyl groups of formula (V) and unreacted hydroxycholesta-5,7-dienes is obtained as the reaction product. Both of them, resulting active-type vitamin $D_3$ compound and unreacted hydroxycholesta-5,7-diene, which have lower alkoxycarbonyl groups as protective groups, are readily separated, as in method (A), by simple recrystallization from or rinsing with an organic solvent, utilizing the difference in solubility between them, without aid of high-speed liquid chromatography, into the active-type vitamin $D_3$ compounds having protected hydroxyl groups and unreacted hydroxycholesta-5,7-dienes.

In the separation, after thermal isomerization, a part of the reaction solvent is distilled off and the solid materials or crystals formed are filtered by a usual method, whereby the hydroxycholesta-5,7-dienes is collected as crystals or solid materials and the active-type vitamin $D_3$ compounds having protected hydroxyl groups is obtained in form of filtrate solution.

Or after thermal isomerization, the reaction solvent is distilled off and as in method A, an alcoholic solvent such as methanol, ethanol, isopropanol, hexanol, cyclohexanol, or the like or a mixture thereof with an ethereal solvent such as diethyl ether, tetrahydrofuran, or the like is added to the residue. The solid materials or crystals formed are subjected to the same operations as in method A, whereby the reaction mixture is similarly separated into active-type vitamin $D_3$ compounds having protected hydroxyl groups and the unreacted hydroxycholesta-5,7-dienes.

The protected active-type vitamin $D_3$ compounds formed by ultraviolet irradiation and thermal isomerization may be partially isomerized to the previtamin $D_3$ compounds at equilibrium reaction, however, the previtamin $D_3$ compounds formed is also separated together with the protected active-type vitamin $D_3$ compounds.

The unreacted hydroxycholesta-5,7-dienes separated is recycled for reuse as a starting material, meanwhile the active-type vitamin $D_3$ compounds having protected hydroxyl groups undergoes the deprotection reaction as in method (A). The reaction of splitting off the protective groups in itself is known and the protective groups are readily removed by contact with an alkali, for example, sodium hydroxide or potassium hydroxide.

The resulting active-type vitamin $D_3$ compounds is purified by a usual method, such as extraction, recrystallization, column chromatography, thin-layer chromatography, high-speed liquid chromatography and others.

Further, in the present invention, high-purity previtamin $D_3$ compounds or active-type vitamin $D_3$ compounds having protected hydroxyl groups is separated from a mixture of the unreacted hydroxycholesta-5,7-dienes and previtamin $D_3$ compounds or a mixture of the unreacted hydroxycholesta-5,7-dienes and active-type vitamin $D_3$ compounds having protected hydroxyl groups resulting from ultraviolet irradiation or combination of ultraviolet irradiation and thermal isomerization, and the high-purity product is provided for the subsequent reactions. Therefore, the final stage of isolation and purification of active-type vitamin $D_3$ compounds is readily effected by a relatively simple method, for example, extraction, recrystallization, chromatography and others.

Consequently, according to the present invention, active-type vitamin $D_3$ compounds, for example, $1\alpha$-hydroxycholecarciferol, $1\alpha,24$-dihydroxycholecarciferol, $1\alpha,25$-dihydrocholecarciferol, which are known as a controller of calcium metabolism in warm-blooded animals, are prepared with industrial advantages.

As mentioned above, in accordance with the present invention, a large amount of an active-type vitamin $D_3$ compounds is efficiently prepared with high industrial advantages by very simple processes comprising of the allylic bromination of a hydroxycholest-5-enes, as a starting material, the dehydrobromination to corresponding hydroxycholesta-5,7-dienes in high yield, an intermediate of active-type vitamin $D_3$ compounds, the subsequent ultraviolet irradiation or a combination of the irradiation and thermal isomerization of the hydroxycholesta-5,7-dienes to a mixture of the unreacted hydroxycholesta-5,7-dienes and previtamin $D_3$ compounds or a mixture of the unreacted hydroxycholesta-5,7-dienes and active-type vitamin $D_3$ compounds having protected hydroxyl groups, the separation of the mixture by very simple operations such as crystallization or rinsing, the recycling of the unreacted hydroxycholesta-5,7-dienes recovered and the final thermal isomerization and protective group splitting off reaction of the remaining compounds, and the process for the preparation of active-type vitamin $D_3$ compounds in the present invention is of very high industrial value, capable of carring out by simple operation and adaptable to large scale commercial production.

This invention is further illustrated by the following detailed examples.

EXAMPLE 1

(1) Synthesis of 1α,3β-diethoxycarbonyloxycholest-5-ene

To a solution of 1α-hydroxycholesterol (10 g) and 4-dimethylaminopyridine (12 g) in methylenechloride (100 ml), was added ethyl chlorocarbonate (47.5 ml) with stirring at 0° C. After stirring for 28 hours at 60° C., the reaction mixture was poured into ice water and extracted with methylenechloride. The methylenechloride extracts were washed with 2 N hydrochloric acid, saturated sodium bicarbonate solution and saturated sodium chloride solution, and dried over anhydrous sodium sulfate. The drying agent was collected on a filter. The filtrate was concentrated under reduced pressure to give 13.34 g of residual product. The crude product was chromatographed on a column of silica gel (300 g) and the column was eluted with benzene-ethylacetate to give 12.6 g (yield: 93%) of 1α,3β-diethoxycarbonyloxycholest-5-ene.

(2) Synthesis of 1α,3β-diethoxycarbonyloxycholesta-5,7-diene

A solution of 1α,3β-diethoxycarbonyloxycholest-5-ene (5.46 g, 10 m moles), dry hexane (100 ml) and 1,3-dibromo-5,5-dimethylhydantoin (1.716 g, 6 m moles) was reacted at the oil bath temperature of 95° C. under the irradiaton of infrared rays for 15 minutes. The reaction mixture was cooled, and the resulting 5,5-dimethylhydantoin and the excessive 1,3-dibromo-5,5-dimethylhydantoin were removed by filtration. The filtrate was concentrated at reduced pressure to afford a residual product. Xylene was added to this substance to form a solution. The resulting solution was added dropwise to a solution held at 170° C. of s-collidine (25 ml) in dry xylene (33 ml), and the reaction was carried out for additional 20 minutes. After the reaction, the hydrobromide of s-collidine was removed by filtration and the filtrate was concentrated under reduced pressure to give residual product. The residue was dissolved in ethyl acetate (200 ml). The ethyl acetate solution was washed with 1 N hydrochloric acid (3×100 ml), saturated sodium bicarbonate and water, and dried over anhydrous sodium sulfate. The drying agent was removed by filtration and the filtrate was concentrated under reduced pressure to give 6.68 g of residual product.

(3) Separation of 1,3-diethoxycarbonyloxycholesta-5,7-diene

The residual product (6.68 g) obtained in (2) above was dissolved in the mixture of methanol (170 ml) and ether (10 ml) with heating at 80° C. The solution was allowed to cool to room temperature and permitted to stay at room temperature over night in the dark to give a white crystalline product. The product was separated by filtration, washed with methanol of 20° C., and dried under the reduced pressure in the dark to afford 3.41 g (62.5%) of crystals as white needles having the following characteristics.

Melting point (from a mixture of ether and methanol): 140.5°–142° C.

IR spectrum, $\nu_{max}^{KBr}$ (cm$^{-1}$): 2950, 2860, 1740, 1465, 1370

NMR spectrum, δ ppm (CDCl$_3$): 0.62 (3H, s, C-18-CH$_3$), 0.86 (6H, d, C-26,27-CH$_3$X2), 1.31 (6H, t, C-1,3-CH$_3$X2 of ethoxycarbonyl groups), 4.20 (4H, q, C-1,3-CH$_2$X2 of ethoxycarbonyl groups), 4.86 (2H, b, C-1,3-HX2), 5.37, 5.67 (2H, b, C-6,7-HX2)

UV spectrum (ethanol, λ$_{max}$, nm): 293 (ε=6760), 281 (ε=11530), 271 (ε=10800), 262 (shoulder ε=7580)

UV spectrum (ether, λ$_{max}$, nm): 293 (ε=7710), 281 (ε=13010), 271 (ε=123600), 262 (shoulder ε=8910).

COMPARATIVE EXAMPLE 1

(1) Synthesis of 1α,3β-diacetoxycholesta-5,7-diene

A soluton of 1α,3β-diacetoxycholest-5-ene (972 mg, 2 m moles), dry hexane (15 ml) and 1,3-dibromo-5,5-dimethyl hydantoin (343 mg, 1.2 m moles) was reacted at the oil bath temperature of 95° C. under the irradiation of infrared rays for 15 minutes. The reaction mixture was cooled, and the resulting 5,5-dimethyl hydantoin and the excessive 1,3-dibromo-5,5-dimethylhydantoin were removed by filtration. The filtrate was concentrated at reduced pressure to afford a residual product. Xylene (6 ml) was added to this substance to form a solution. The resulting solution was added dropwise to a solution held at 170° C. of s-collidine (5 ml) in dry xylene (6 ml), and the reaction was carried out for additional 20 minutes. After the reaction, the hydrobromide of s-collidine was removed by filtration and filtrate was concentrated under reduced pressure to give residual product. The residue was dissolved in ethyl acetate (30 ml). The ethyl acetate solution was washed with 1 N hydrochloric acid (2×10 ml), saturated sodium bicarbonate and water, and dried over anhydrous sodium sulfate. The drying agent was removed by filtration and the filtrate was concentrated under reduced pressure to give 908 mg of residual product.

(2) Separation of 1α,3β-diacetoxycholesta-5,7-diene

The residue (908 mg, 1α,3β-diacetoxycholesta-5,7-diene: 1α,3β-diacetoxycholesta-4,6-diene÷2:1, from the UV spectrum) was dissolved in the mixture of ether-hexane (1:10) with heating, allowed to cool to room temperature for 30 minutes, and permitted to stand in the dark at a temperature of 5° C. for 14 hours. After standing, the solvent was removed by decontation, and the oily product was obtained, and washed with a cooled methanol, but not to afford a crystal. In the obtained oily product, the ratio of 5,7-diene to 4,6-diene was 2:1.

EXAMPLE 2

(1) Synthesis of 1α,3β-diethoxycarbonyloxycholesta-5,7-diene

To a solution of 1α,3β-diethoxycarbonyloxycholest-5-ene (2.73 g, 5 m moles) in dry hexane (50 m), 1,3-dibromo-5,5-dimethylhydantoin (858 mg, 3 m moles) was added dropwise under stirring and heating at oil bath temperature of 95° C., and the mixture was continued to react under the irradiation of infrared rays for 15 minutes. The reaction mixture was cooled, and the resulting precipitate was removed by filtration, the filtrate was concentrated at reduced pressure at 40° C. to afford a residual product. Xylene was added to this substance to form a solution. The resulting solution was added dropwise to a solution held at 170° C. of s-collidine (12.5 ml) in dry xylene (16.5 ml), and the reaction was carried out for additional 20 minutes. After the reaction, the resulting precipitate was removed by filtration and the filtrate was concentrated under reduced pressure at 40°

C. to give a residual product. The product was dissolved in ethyl acetate (100 ml). The ethylacetate solution was washed with 1 N hydrochloric acid (3×50 ml), saturated sodium bicarbonate and water, and dried over anhydrous sodium sulfate. The drying agent was removed by filtration and the filtrate was concentrated under reduced pressure to give 3.04 g of residual product.

(2) Analysis of 1α,3β-diethoxycarbonyloxycholesta-5,7-diene

The product (3.04 g) obtained in (1) above was dissolved in ether (10 l). The resulting solution was subjected to the measurement of UV spectrum with a spectrophotometer (cell length; 1 cm, wavelength; 340 nm-200 nm). The UV spectrum showed, as maximum absorbance ($\lambda_{max}$), 293, 281, 271, 260 (shoulder), 249.4 (shoulder), 241 and 232. From the calculation based on the value of $\lambda_{max}$(281, $\epsilon$10250), the reaction yield in the step (1) above was determined to be 78.8%. On the other hand, from the ratio of absorbance in $\lambda_{max}$; 281 and $\lambda_{max}$; 240, the ratio ($\Delta 5,7/\Delta 4,6$) of 1α,3β-diethoxycarbonyloxycholesta-5,7-diene to 1α,3β-diethoxycarbonyloxycholesta-4,6-diene was 5.25

COMPARATIVE EXAMPLE 2

(1) Synthesis of 1α,3β-diacetoxycholesta-5,7-diene

To a solution of 1α,3β-diacetoxycholest-5-ene (2.43 g, 5 m moles) in dry hexane (50 ml), 1,3-dibromo-5,5-dimethylhydantoin (858 mg, 3 m moles) was added dropwise under stirring and heating at oil bath temperature of 95° C., and the resulting mixture was continued stirring for 15 minutes under the irradiation of infrared rays. The reaction mixture was cooled, the precipitate filtered, and washed with hexane, and filtrate and washings were combined to give after evaporation of all solvents a residual product. Xylene was added to this substance to form a solution.

The resulting solution was added dropwise to a solution held at 170° C. of s-collidine (12.5 ml) in dry xylene (16.5 ml), and the reaction was carried out for additional 20 minutes. The reaction mixture was cooled, the precipitate filtered, and washed with hexane, and filtrate and washings were combined. The combined solution was evaporate to afford a residual product. The residue was dissolved in ethylacetate (100 ml), washed with 1 N hydrochloric acid (3×50 ml), saturated sodium bicarbonate and water, and dried over anhydrous sodium sulfate. The drying agent was removed by filtration and the filtrate was concentrated under reduced pressure to give 2.42 g of the crude product.

(2) Analysis of 1α,3β-diacetoxycholesta-5,7-diene

The product (2.42 g) obtained in (1) above was dissolved in ether (10 l). The resulting solution was subjected to the measurement of UV spectrum with a spectrophotometer (cell length; 1 cm, wavelength; 340 nm-200 nm). The UV spectrum showed, as maximum absorbance ($\lambda_{max}$), 293.5, 281, 271, 260 (shoulder), 249, 239 and 228. From the value of $\lambda_{max}$ (281, $\epsilon$=8350), the reaction yield in the step (1) above was determined to be 64.2%. On the other hand, from the ratio of absorbance in $\lambda_{max}$; 281 and 239, the ratio ($\Delta 5.7/\Delta 4.6$) was 3.23.

EXAMPLE 3

(1) Synthesis of 1α,3β-dimethoxycarbonyloxycholesta-5,7-diene

To a solution of 1α,3β-dimethoxycarbonyloxycholest-5-ene (518 mg, 1 m mole) in dry hexane (10 ml), 1,3-dibromo-5,5-dimethylhydantoin (172 mg, 0.6 m moles) was added dropwise under stirring and heating at oil bath temperature of 95° C., and the mixture was continued to react under the irradiation of infrared rays for 15 minutes. The reaction mixture was cooled, and the resulting precipitate was removed by filtration, the filtrate was concentrated at reduced pressure at 40° C. to afford a residual product. Xylene was added to this substance to form a solution. The resulting solution was added dropwise to a solution held at 170° C. of s-collidine (2.5 ml) in dry xylene (3 ml), and the reaction was carried out for additional 20 minutes. After the reaction, the resulting precipitate was removed by filtration and the filtrate was concentrated under reduced pressure at 40° C. to give residual product. The product was dissolved in ethylacetate (20 ml). The ethylacetate solution was washed with 1 N hydrochloric acid (3×10 ml), saturated sodium bicarbonate and water, and dried over anhydrous sodium sulfate. The drying agent was removed by filtration and the filtrate was concentrated under reduced pressure to give 479 mg of residual product.

(2) Analysis of 1α,3β-dimethoxycarbonyloxycholesta-5,7-diene

The product (479 mg) obtained in (1) above was dissolved in ether (10 l). The resulting solution was subjected to the measurement of UV spectrum with a spectrophotometer (cell length; 1 cm, wavelength; 340 nm-200 nm). The UV spectrum showed, as maximum absorbance ($\lambda_{max}$), 293, 281, 271, 260 (shoulder), 249.5 (shoulder), 241 and 232. From the ratio of absorbance in $\lambda_{max}$; 281 and 240, the ratio ($\Delta 5,7/\Delta 4,6$) 1α,3β-dimethoxycarbonyloxycholesta-5,7-diene to 1α,3β-dimethoxycarbonyloxycholesta-4,6-diene was 4.34.

EXAMPLE 4

(1) Synthesis of 1α,3β-diethoxycarbonyloxy-25-hydroxycholesta-5,7-diene

To a solution of 1α,3β-diethoxycarbonyloxy-25-hydroxycholesta-5-ene (562 mg, 1 m mole) in dry hexane (10 m), 1,3-dibromo-5,5-dimethylhydantoin (172 mg, 0.6 m moles) was added dropwise under stirring and heating at oil bath temperature of 95° C., and the mixture was continued to react under the irradiation of infrared rays for 15 minutes. The reaction mixture was cooled, and the resulting precipitate was removed by filtration, the filtrate was concentrated at reduced pressure at 40° C. to afford a residual product. Xylene was added to this substance to form a solution. The resulting solution was added dropwise to a solution held at 170° C. of s-collidine (2.5 ml) in dry xylene (3 ml), and the reaction was carried out for additional 20 minutes. After the reaction, the resulting precipitate was removed by filtration and the filtrate was concentrated under reduced pressure at 40° C. to give residual product. The product was dissolved in ethylacetate (20 ml). The ethylacetate solution was washed with 1 N hydrochloric acid (3×10 ml), saturated sodium bicarbonate and water, and dried over anhydrous sodium sulfate. The drying agent was removed by filtration and the filtrate was concentrated under reduced pressure to give 482 mg of residual product.

(2) Analysis of 1,3-diethoxycarbonyloxy-25-hydroxycholesta-5,7-diene

The product (482 g) obtained in (1) above was dissolved in ether (10 l). The resulting solution was subjected to the measurement of UV spectrum with a spectrophotometer (cell length; 1 cm, wavelength; 340 nm-200 nm). The UV spectrum showed, as maximum absorbance ($\lambda_{max}$), 293, 281, 271, 260 (shoulder), 249.5 (shoulder), 241 and 232. From the ratio of absorbance in $\lambda_{max}$; 281 and 240, the ratio ($\Delta 5,7/\Delta 4,6$) of $1\alpha,3\beta$-diethoxycarbonyloxy-25-hydroxycholesta-5,7-diene to $1\alpha,3\beta$-diethoxycarbonyloxy-25-hydroxycholesta-4,6-diene was 4.36.

COMPARATIVE EXAMPLE 3

(1) Synthesis of $1\alpha,3\beta,25$-triacetoxycholesta-5,7-diene

To a solution of $1\alpha,3\beta,25$-triacetoxycholest-5-ene (544 mg, 1 m mole) in dry hexane (10 m), 1,3-dibromo-5,5-dimethylhydantoin (172 mg, 0.6 m moles) was added dropwise under stirring and heating at oil bath temperature of 95° C., and the mixture was continued to react under the irradiation of infrared rays for 15 minutes. The reaction mixture was cooled, and the resulting precipitate was removed by filtration, the filtrate was concentrated at reduced pressure at 40° C. to afford a residual product. Xylene was added to this substance to form a solution. The resulting solution was added dropwise to a solution held at 170° C. of s-collidine (2.5 ml) in dry xylene (3 ml), and the reaction was carried out for additional 20 minutes. After the reaction, the resulting precipitate was removed by filtration and the filtrate was concentrated under reduced pressure at 40° C. to give residual product. The product was dissolved in ethylacetate (20 ml). The ethylacetate solution was washed with 1 N hydrochloric acid (3×10 ml), saturated sodium bicarbonate and water, and dried over anhydrous sodium sulfate. The drying agent was removed by filtration and the filtrate was concentrated under reduced pressure to give 473 mg of residual product.

(2) Analysis of $1\alpha,3\beta,25$-triacetoxycholesta-5,7-diene

The product (473 mg) obtained in (1) above was dissolved in ether (10 l). The resulting solution was subjected to the measurement of UV spectrum with a spectrophotometer (cell length; 1 cm, wavelength; 340 nm-200 nm). The UV spectrum showed, as maximum absorbance ($\lambda_{max}$), 293, 281, 271, 260 (shoulder), 249.5 (shoulder), 241 and 232. From the ratio of absorbance in $\lambda_{max}$; 281 and 240, the ratio ($\Delta 5,7/\Delta 4,6$) of $1\alpha,3\beta,25$ triacetoxycholesta-5,7-diene to $1\alpha,3\beta,25$-triacetoxycholesta-4,6-diene was 2.57.

EXAMPLE 5

(1) Synthesis of $1\alpha,3\beta,24(R)$-triethoxycarbonyloxycholest-5-ene

A ethyl chlorocarbonate (24.75 ml) was added dropwise to a solution of $1\alpha,3\beta,24(R)$-trihydroxycholest-5-ene (3.63 g), 4-dimethylaminopyridine (6.25 g) and methylenechloride (40 ml) with stirring at 0° C. After stirring for 27 hours at 60° C., the reaction mixture was poured into ice water and extracted with methylenechloride. The extracts were washed with 2 N hydrochloric acid, saturated sodium bicarbonate solution and saturated sodium chloride solution, and dried over anhydrous sodium sulfate. The drying agent was removed by filtration and the filtrate was concentrated under reduced pressure to give 4.98 g of residual product. The residue was recrystallized from methanol (10 ml) to afford 3.64 g of $1\alpha,3\beta,24(R)$-triethoxycarbonyoxycholest-5-ene as crystals.

(2) Synthesis of $1\alpha,3\beta,24(R)$-triethoxycarbonyloxycholesta-5,7-diene

A solution of $1\alpha,3\beta,24(R)$-triethoxycarbonyloxycholest-5-ene (3.49 g, 5.5 m moles), dry hexane (58 ml) and 1,3-dibromo-5,5-dimethylhydantoin (998 mg, 3.3 m moles) was boiled under the irradiation of infrared rays for 15 minutes. The reaction mixture was cooled, and the resulting 5,5-dimethylhydantoin and the excessive 1,3-dibromo-5,5-dimethylhydantoin were removed by filtration. The filtrate was concentrated at reduced pressure to afford a residual product. Xylene was added to this substance to form a solution. The resulting solution was added dropwise to a solution held 170° C. of s-collidine (14.5 ml) in dry xylene (19 ml), and the reaction was carried out for additional 20 minutes. After the reaction, the hydrobromide of s-collidine was removed by filtration and the filtrate was concentrated under reduced pressure at 40° C. to give residual product. The residue was dissolved in ethylacetate (200 ml). The organic phase was washed with 1 N hydrochloric acid (3×10 ml), saturated sodium bicarbonate solution and water, and dried over anhydrous sodium sulfate. The drying agent was removed by filtration and the filtrate was concentrated under reduced pressure to give 3.68 g of residual product.

(3) Separation of $1\alpha,3\beta,24(R)$-triethoxycarbonyloxycholesta-5,7-diene

The residual product (3.68 g) obtained in (2) above was dissolved in the mixture of methanol (7 ml) and ether (1 ml) with heating. The solution was allowed to cool to 5° C. in the dark. The resulting product were collected by filtration, and dissolved in methanol (13 ml) with heating at 70° C. for 30 minutes. The solution was cooled to room temperature, and moreover allowed to stand in the dark at 5° C. for 1.5 hours to afford crystals as white needles. The crystals were collected by filtration, washed with methanol of 20° C., and dried under the reduced pressure in the dark to give 1.69 g (48.5%) of crystals as colorless needles having the following characteristics.

Melting point (from methanol): 116°–117° C.

UV spectrum (ethanol, $\lambda_{max}$, nm): 262 (8110), 271 (11410), 281 (12130), 293 (7200)

NMR spectrum, $\delta$ ppm CDCl$_3$): 0.62 (3H, s, C-18-CH$_3$), 1.31 (9H, t, C-1,3 and 24-CH$_3$x3 of ethoxycarbonyl), 4.18 (6H, q, c-1,3 and 24-CH$_2$x3 of ethoxycarbonyl), 4.50 (1H, bm, C-24-H), 4.80 (2H, bm, C-1,3-Hx2), 5.35, 5.65 (2H, bm, C-6-H and C-7-H).

EXAMPLE 6

(1) Synthesis of $1\alpha$-ethoxycarbonyloxyprecholecalciferol-$3\beta$-ethoxycarbonate 272 mg (0.5 m moles) of $1\alpha,3\beta$-diethoxycarbonyloxycholesta-5,7-diene was dissolved in 600 ml of diethyl ether, and this solution was irradiated with ultraviolet rays for 5 minutes at 10° C. in an atmosphere of argon using a 200 W high pressure mercury lamp, 654A-36, trademark for a product of Hanovia Company, (Convertion 28%).

After the reaction, the ether solution was evaporated off at room temperature under reduced pressure to give a residual product. Methyl alcohol (20 ml) cooled at 0° C. was added to the residue. The residue was suspended to afford crystals, and the resulting crystals, 173 mg of 1α,3β-diethoxycarbonyloxycholesta-5,7-diene, were removed by filtration. The filtrate was concentrated at 25° C. under reduced pressure to afford the oily residue containing 1α-ethoxycarbonyloxyprecholecalciferol-3β-ethoxycarbonate. This product was used as the starting material in the next step without purification.

(2) Synthesis of 1α-ethoxycarbonyloxycholecalciferol-3β-ethoxycarbonate

1α-ethoxycarbonyloxyprecholecalciferol-3β-ethoxycarbonate obtained in (1) above, was dissolved in 100 ml of benzene, and isomerization was carried out for 14 hours at 50° C. in an atmosphere of argon. After the reaction, the benzene was evaporated off at 25° C. under reduced pressure to afford the oily residue containing 1α-ethoxycarbonyloxycholecalciferol-3β-ethoxycarbonate. This crude product was used as the starting material in the next step (3) without purification.

(3) Synthesis of 1α-hydroxy cholecalciferol

1α-ethoxycarbonyloxy cholecalciferol-3β-ethoxycarbonate described above was dissolved in a mixture of 5 ml of methyl alcohol and 5 ml of benzene, and 5 ml of 2 N-methyl alcohol solution of potassium hydroxide was added dropwise. After the addition, the reaction was carried out at 60° C. for 1 hour.

The reaction mixture was concentrated at 25° C. under reduced pressure to afford a residual product. 50 ml of water was then added to the residue and the product was extracted with ethyl acetate (50 ml×2). The ethyl acetate extracts were combined, washed with a dilute hydrochloric acid, a saturated aqueous solution of sodium carbonate and a saturated aqueous solution of sodium chloride, dried over anhydrous sodium sulfate, filtered, and evaporated off at reduced pressure to afford 76 mg of the oily residue containing 1α-hydroxycholecalciferol. This crude product was column-chromatographed using silica gel (eluted with a benzeneacetone mixed solvent) to afford 22 mg of 1α-hydroxycholecalciferol (yield; 30%, based on 99 mg of 1α,3β-diethoxycarbonyloxycholesta-5,7-diene used up).

This product showed the same characteristics as an authentic 1α-hydroxycholecalciferol.

Melting point: 140°–141° C. (from a mixture of ether and n-hexane)

IR spectrum, $\nu_{max}^{KBr}$ (cm$^{-1}$): 3400, 2950, 2890, 1640, 1630, 1470, 1450, 1380, 1055, 895, 795

NMR spectrum, δ ppm (CDCl$_3$): 0.55 (3H, s, C-18-CH$_3$), 0.87 (6H, d, J=6.4 Hz, C-26 and 27-CH$_3$X2), 0.93 (3H, d, J=4.8 Hz, C-21-CH$_3$), 4.22–4.45 (2H, m, 1β-and 3α-proton), 5.00, 5.33 (1H, 1H, s, s, C-19-2H, vinyl proton), 5.95, 6.44 (1H, 1H, d, J=11.5 Hz, C-6-H, C-7-H), Mass spectrum: M+ 400, 382, 364, 349, 287, 269, 251.

EXAMPLE 7

(1) Synthesis of 1α-ethoxycarbonyloxyprecholecalciferol-3β-ethoxycarbonate

(a) The first reaction 272 mg (0.5 m moles) of 1α,3β-diethoxycarbonyloxycholesta-5,7-diene was dissolved in 600 ml of diethyl ether, and this solution was irradiated with ultraviolet rays for 5 minutes at 10° C. in an atmosphere of argon using a 200 W. high pressure mercury lamp, 654A-36, trademark for a product of Hanovia Company (conversion: 30%)

After the reaction, the ether solution was evaporated off at room temperature under reduced pressure.

Using a 272 mg (0.5 m moles) of 1α,3β-diethoxycarbonyloxycholesta-5,7-diene, the same reaction as mentioned above was conducted three times.

The obtained residues in these reaction were put together, and methyl alcohol (80 ml) cooled at 0° C. was added to the residues.

The residue was suspended to afford crystals and the resulting crystals, 664 mg of 1α,3β-diethoxycarbonyloxycholesta-5,7-diene, were removed by filtration.

The filtrate was concentrated at 25° C. under reduced pressure to afford the oily residue containing 1α-ethoxycarbonyloxy-pre-cholecalciferol-3β-ethoxycarbonate. This residue was named as L-No.1.

(b) The second reaction 120 mg of 1α,3β-diethoxycarbonyloxycholesta-5,7-diene recovered in the first reaction (a) was dissolved in 600 ml of diethyl ether, and this solution was irradiated with ultraviolet rays for 2.5 minutes at 10° C. in an atmosphere of argon using a 200 W high pressure mercury lamp, 654 A-36 trademark for a product of Hanovia Company (conversion; 30%).

After the reaction, the ether solution was evaporated off at room temperature under reduced pressure.

544 mg (1 m mol) of 1α,3β-diethoxycarbonyloxycholesta-5,7-diene, the remains of 1α,3β-diethoxycarbonyloxy cholesta-5,7-diene recovered in the first step (a), was irradiated with two batches in the same way as described in the first reaction (a). The obtained residues in these reaction were put together, and methyl alcohol (50 ml) cooled at 0° C. was added.

The residue was suspended to afford crystals, and the resulting crystals, 358 mg of 1α,3β-diethoxycarbonyloxycholesta-5,7-diene were removed by filtration.

The filtrate was concentrated at 25° C. under reduced pressure to afford the oily residue containing 1α-ethoxycarbonyloxy-pre-cholecalciferol-3β-ethoxycarbonate. This residue was named as L-No.2

(c) The third reaction 358 mg of 1α,3β-diethoxycarbonyloxycholesta-5,7-diene recovered in the second reaction (b) was dissolved in 600 ml of diethyl ether, and this solution was irradiated with ultraviolet rays for 5 minutes at 10° C. in an atmosphere of argon using a 200 W high pressure mercury lamp, 654A-36 trademark for a product of Hanovia Company (conversion; 30%).

After the reaction, the ether solution was evaporated off at room temperature under reduced pressure to afford a residual product.

To the residue methyl alcohol (25 ml) cooled at 0° C. was added.

The residue was suspended to afford crystals and the resulting crystals, 224 mg of 1α,3β-diethoxycarbonyloxycholesta-5,7-diene, were removed by filtration.

After the filtration, the filtrate was concentrated at 25° C. under reduced pressure to afford the oily residue containing 1α-ethoxycarbonyloxyprecholecalciferol-3β-ethoxycarbonate. This residue was named as L-No.3.

(d) The fourth reaction 224 mg of 1α,3β-diethoxycarbonyloxycholesta-5,7-diene recovered in the third reaction (c) was dissolved in 600 ml of diethyl ether, and this solution was irradiated with ultraviolet rays for 10 minutes at 10° C. in an atmosphere of argon using a 200 W high pressure mercury lamp, 654A-36 trademark for a product of Hanovia Company (conversion: 60%, at the final reaction, the remained hydroxycholesta-5,7-diene was converted to the previtamin D$_3$ compound as much as possible).

After the reaction, the ether solution was evaporated off at room temperature under reduced pressure to afford the oily residue containing 1α-ethoxycarbonyloxy-pre-cholecalciferol-3β-ethoxycarbonate.

This residue was named as L-No.4.

(2) Synthesis of 1α-ethoxycarbonyloxycholecalciferol-3β-ethoxycarbonate

The residues described above, containing 1α-ethoxycarbonyloxyprecholecalciferol-3β-ethoxycarbonate L-No.1~No.4, were put together and dissolved in 400 ml of benzene, and isomerization was carried out for 7 hours at 60° C. in an atmosphere of argon.

After the reaction, the benzene solution was evaporated off at 25° C. under reduced pressure to afford the oily residue containing 1α-ethoxycarbonyloxycholecalciferol-3β-ethoxycarbonate. This crude product was used as the starting material in the next step (3) without purification.

(3) Synthesis of 1α-hydroxycholecalciferol

1α-ethoxycarbonyloxycholecalciferol-3β-ethoxycarbonate obtained in (2) above, was dissolved in a mixture of 20 ml of methyl alcohol and 20 ml of benzene, and 20 ml of 2 N-methyl alcohol solution of potassium hydroxide was added dropwise to the mixture.

After the addition, the reaction was carried out at 60° C. for 1 hour.

After the reaction, the reaction mixture was concentrated at 25° C. under reduced pressure to afford a residual product. 200 ml of water was then added to the residue and the product was extracted with ethyl acetate (200 ml×2). The ethyl acetate extracts were combined, washed with a dilute hydrochloric acid, a saturated aqueous solution of sodium carbonate and a saturated aqueous solution of sodium chloride, dried over anhydrous sodium sulfate, filtered and evaporated off at reduced pressure to afford 684 mg of the oily residue containing 1α-hydroxycholecalciferol. This crude product was column-chromatographed using silica gel (eluted with a benzene-acetone mixed solvent) to afford 275 mg of 1α-hydroxycholecalciferol (yield: 34%).

Analysis of the product showed the following results.
Melting point: 141.5° to 142° C.
UV spectrum: $\lambda_{max}^{ethanol}$ 265 nm ($\epsilon = 17200$)

High resolution mass spectrum: M+400.3358 ($C_{27}H_{44}O_2$)

EXAMPLE 8

(1) Synthesis of 1α-ethoxycarbonyloxycholecalciferol-3β-ethoxycarbonate 272 mg (0.5 m mol) of 1α,3β-diethoxycarbonyloxycholesta-5,7-diene was dissolved in 600 ml of diethyl ether, and this solution was irradiated with ultraviolet rays for 5 minutes at 10° C. in an atmosphere of argon using a 200 W high pressure mercury lamp, 654A-36 trademark for a product of Hanovia Company, (conversion 30%).

After the reaction, the ether solution was evaporated off at room temperature under reduced pressure to afford a residual product. 272 mg (0.5 m mol) of 1α,3β-diethoxycarbonyloxycholesta-5,7-diene was irradiated in the same way as described above.

The obtained residues in these reaction were put together, dissolved in 200 ml of benzene, and isomerization was carried out for 3 hours at 70° C. in an atmosphere of argon. After the reaction, the benzene solution was evaporated off at 25° C. under reduced pressure to afford the residue containing 1α-ethoxycarbonyloxycholecalciferol-3β-ethoxycarbonate.

Methyl alcohol (40 ml) cooled at 0° C. was added to the residue. The residue was suspended to afford crystals and the resulting crystals, 286 mg of 1α,3β-diethoxycarbonyloxycholesta-5,7-diene, were removed by filtration. After the filtration, the filtrate was concentrated at 25° C. under reduced pressure to afford the oily residue containing 1α-ethoxycarbonyloxycholecalciferol-3β-ethoxycarbonate. This crude product was used as the starting material in the next step (2) without purification.

(2) Synthesis of 1α-hydroxycholecalciferol

1α-ethoxycarbonyloxycholecalciferol-3β-ethoxycarbonate obtained above, was dissolved in a mixture of 10 ml of methyl alcohol and 10 ml of benzene, and 10 ml of 2 N-methyl alcohol solution of potassium hydroxide was added dropwise to the mixture. After the addition, the reaction was carried out at 60° C. for 1 hour.

The reaction mixture was concentrated at 25° C. under reduced pressure to afford a residual product. 100 ml of water was then added to the residue and the product was extracted with ethyl acetate (100 ml×3). The ethylacetate extracts were combined, washed with a dilute hydrochloric acid, a saturated aqueous solution of sodium carbonate and a saturated aqueous solution of sodium chloride, dried with anhydrous sodium sulfate, filtered and evaporated off at reduced pressure to afford 200 mg of the oily residue containing 1α-hydroxycholecalciferol.

This crude product was column-chromatographed using silica gel (eluted with a benzene-acetone mixture solvent) to afford 57 mg of 1α-hydroxycholecalciferol (yield 30%, based on 258 mg of 1α,3β-diethoxy carbonyloxycholesta-5,7-diene used up). This product showed the same characteristics as an authentic 1α-hydroxycholecarciferol.

COMPARATIVE EXAMPLE 4

(1) Synthesis of 1α-acetoxyprecholecalciferol-3β-acetate

A solution of 1α,3β-diacetoxycholesta-5,7-diene (242 mg, 0.5 m moles) in benzene (600 ml) was cooled, and irradiated for 22 minutes (conversion÷60%) under argon using a 200 W high pressure mercury lamp, 654A-36, trademark for a product of Hanovia Company. The resulting solution was concentrated under the reduced pressure at 25° C. to afford a residual product. Using a 1α,3β-diacetoxycholesta-5,7-diene (1.21 g, 25 m moles), the same reaction as mentioned above was conducted five times. The obtained residual products were combined, and subjected to the next reaction without purification.

(2) Synthesis of 1α-acetoxycholecalciferol-3β-acetate

A solution of 1α-acetoxyprecholecalciferol-3β-acetate obtained in (1) above in benzene (800 ml) was heated at a bath temperature of 80° C. for 2.5 hours under an atmosphere of argon. After the reaction, the solution was concentrated under the reduced pressure to afford an oily product containing 1α-acetoxyprecholecalciferol-3β-acetate. The oily product, without the purification, subjected to the next reaction.

(3) Synthesis of 1α-hydroxycholecalciferol

To a solution of the oily product obtained in (2) above in methanol, 2.5% potassium hydroxide (11.2 ml) was added dropwise at the room temperature with stirring, and the reaction was carried out at the room temperature for an additional 2 hours. After the reaction, the resulting mixture was concentrated under the reduced pressure at 25° C. to afford a residual product. Water (62 ml) was then added to the residue and the product was extracted with ether (2×120 ml). The ether extracts were combined, washed with sodium chloride solution, dried over anhydrorous sodium sulfate, filtrated and concentrated under reduced pressure 2.1 g of oily product. The product was chromatographed on a column of silica gel (Wokogd C-200, 75 g) and the column was eluted with benzene-ethyl acetate to give 233 mg (yield; 19.5%, based on 1α,3β-diacetoxycholesta-5,7-diene) of 1α-hydroxycholecalciferol.

COMPARATIVE EXAMPLE 5

(1) Synthesis of 1α-acetoxycholecalciferol-3β-acetate 242 mg (0.5 m mol) of 1α,3β-diacetoxycholesta-5,7-diene was dissolved in 600 ml of diethyl ether, and this solution was irradiated with ultraviolet rays for 5 minutes at 10° C. in an atmosphere of argon using a 200 W high pressure mercury lamp, 654A-36 trademark for a product of Hanovia Company, (conversion 30%).

After the reaction, the ether solution was evaporated off at room temperature under reduced pressure to afford a residual product. Moreover 242 mg (0.5 m mol) of 1α,3β-diacetoxycholesta-5,7-diene was irradiated in the same way as described above.

The obtained residues in these reaction were put together, dissolved in 200 ml of benzene, and isomerization was carried out for 3 hours at 70° C. in an atmosphere of argon. After the reaction, the benzene solution was evaporated off at 25° C. under reduced pressure to afford the residue containing 1α-acetoxycholecalciferol-3β-acetate.

Methyl alcohol (40 ml) cooled at 0° C. was added to the residue. The residue was subjected to suspension but not to afford crystals, and 1α,3β-diacetoxycholesta-5,7-diene could not be recovered.

What we claim is:

1. A process for preparing a hydroxycholesta-5,7-diene of the following formula [II]

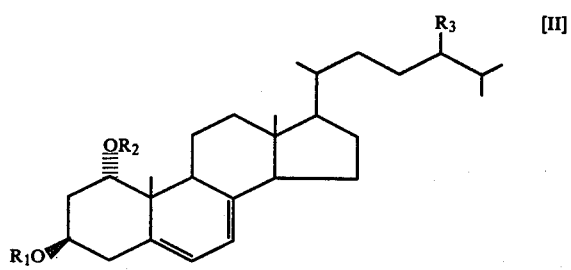

wherein $R_1$ and $R_2$ represent a lower alkoxycarbonyl group, $R_3$ represents a hydrogen atom or a lower alkoxycarbonyloxy group, which consists essentially of reacting a hydroxycholest-5-ene of the following formula [I]

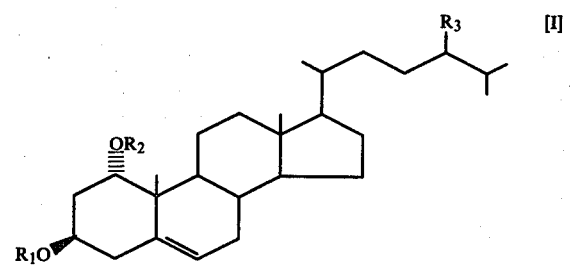

Wherein $R_1$, $R_2$ and $R_3$ are the same as defined above, with an allylic brominating agent in an inert organic solvent, and then contacting the resulting reaction mixture with a dehydrobrominating agent to form a mixture of the hydroxycholesta-5,7-diene of the following formula [II]

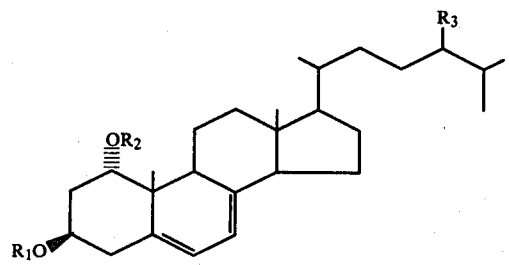

wherein $R_1$, $R_2$ and $R_3$ are the same as defined above, and a hydroxycholesta-4,6-diene of the following formula

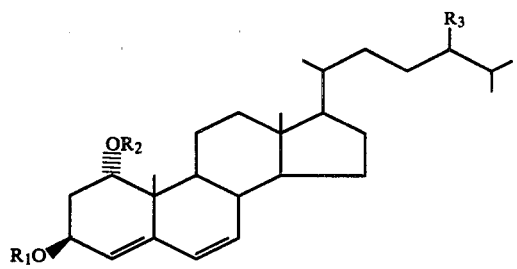

wherein $R_1$, $R_2$ and $R_3$ are the same as defined above, and separating the mixture by means of recrystallization to obtain the pure hydroxycholesta-5,7-diene.

2. The process of claim 1 wherein $R_1$ and $R_2$ in the hydroxycholest-5-ene of formula [I] are a methoxycarbonyl or an ethoxycarbonyl group.

3. A process for preparing an active-type vitamin $D_3$ compound of the following formula [IV]

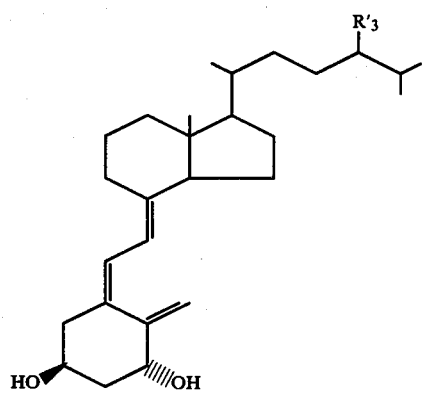

where $R_3'$ represent a hydrogen atom or a hydroxyl group, which consists essentially of:

(i) reacting a hydroxycholesta-5-ene of the following formula [I]

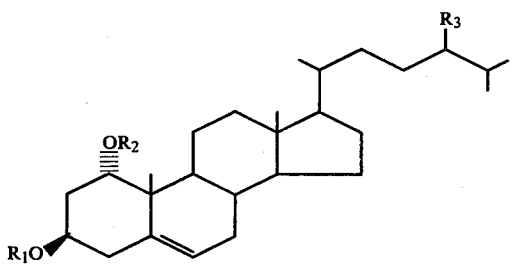

wherein $R_1$ and $R_2$ represent a lower alkoxycarbonyl group, $R_3$ represents a hydrogen atom or a lower alkoxycarbonyloxy group, with an allylic brominating agent in an inert organic solvent, and then contacting the resulting reaction mixture with a dehydrobrominating agent to form a mixture of a hydroxycholesta-5,7-diene of the following formula [II]

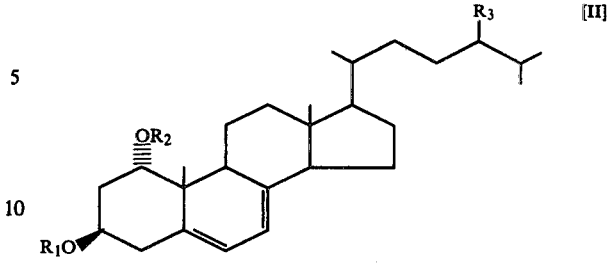

wherein $R_1$, $R_2$ and $R_3$ are the same as defined above and a hydroxycholesta-4,6-diene of the following formula

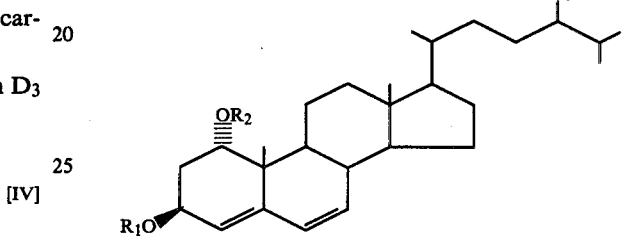

wherein $R_1$, $R_2$ and $R_3$ are the same as defined above;

(ii) separating the mixture by means of recrystallization to obtain the pure hydroxycholesta-5,7-diene;

(iii) exposing the hydroxycholesta-5,7-diene of formula [II] to ultraviolet irradiation in an inert organic solvent to obtain a mixture of previtamin $D_3$ compound of the following formula [III]

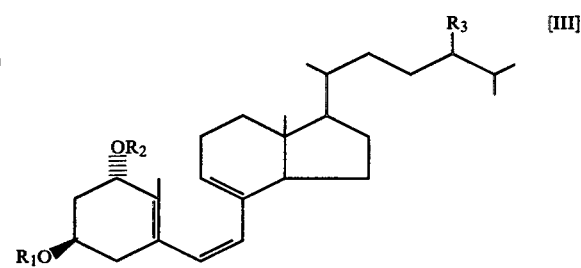

wherein $R_1$, $R_2$ and $R_3$ are the same as defined above, and the unchanged hydroxycholesta-5,7-diene;

(iv) separating the mixture by means of recrystallization or rinse into the previtamin $D_3$ compound, and the unchanged hydroxycholesta-5,7-diene;

(v) recycling the unchanged hydroxycholesta-5,7-diene through the ultraviolet irradiation; and (vi) thermally isomerizing the previtamin $D_3$ compound and splitting off the protective groups.

4. The process of claim 3, wherein $R_1$ and $R_2$ in the hydroxycholest-5-ene of formula [1] are an ethoxycarbonyl or a methoxycarbonyl group.

5. The process of claim 3 wherein the exposing of hydroxycholesta-5,7-diene to ultraviolet irradiation is conducted until the conversion of the hydroxycholesta-5,7-diene reaches 0.1–50%.

6. A process for preparing an active-type vitamin $D_3$ compound of the following formula [IV]

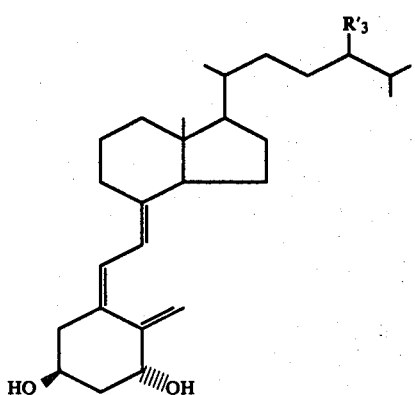

wherein $R_3'$ represent a hydrogen atom or a hydroxyl group, which consists essentially of:

(i) reacting a hydroxycholesta-5-ene of the following formula [I]

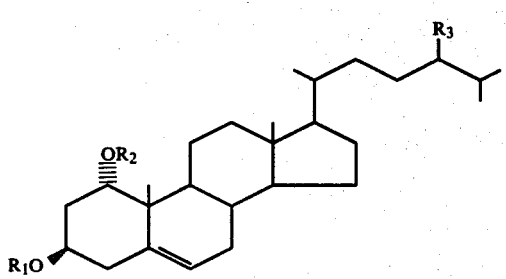

wherein $R_1$ and $R_2$ represent a lower alkoxycarbonyl group, $R_3$ represents a hydrogen atom or a lower alkoxycarbonyloxy group, with an allylic brominating agent in an inert organic solvent, and then contacting the resulting reaction mixture with a dehydrobrominating agent to form a mixture of a hydroxycholesta-5,7-diene of the following formula [II]

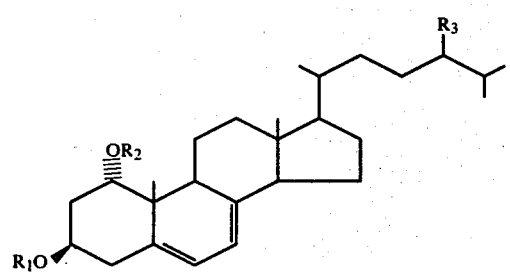

wherein $R_1$, $R_2$ and $R_3$ are the same as defined above and a hydroxycholesta-4,6-diene of the following formula

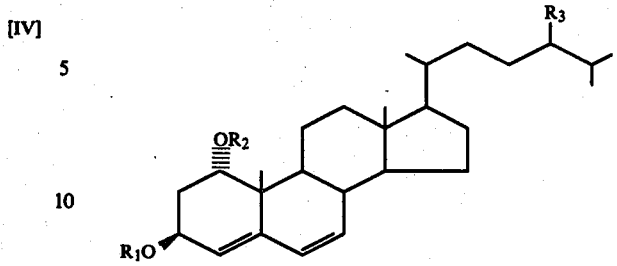

wherein $R_1$, $R_2$ and $R_3$ are the same as defined above (ii) separating the mixture by means of recrystallization to to obtain the pure hydroxycholesta-5,7-diene;

(iii) exposing the hydroxycholesta-5,7-diene of the formula [II] to ultraviolet irradiation in an inert organic solvent, then thermally isomerizing to obtain a mixture of protected active-type vitamin $D_3$ compound of the following formula [V]

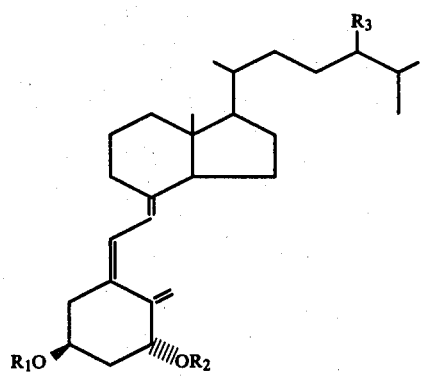

wherein $R_1$, $R_2$ and $R_3$ are the same as defined above, and the unchanged hydroxycholesta-5,7-diene of the formula [II];

(iv) separating the mixture by means of recrystallization or rinse into the protected active-type vitamin $D_3$ compound and the unchanged hydroxycholesta-5,7-diene;

(v) recycling the unchanged hydroxycholesta-5,7-diene through the ultraviolet irradiation; and (vi) splitting off the protective groups of the protected active-type vitamin $D_3$ compound.

7. The process of claim 6 wherein $R_1$ and $R_2$ in the hydroxycholest-5-ene of formula [I] are an ethoxycarbonyl or a methoxycarbonyl group.

8. The process of claim 6 wherein the exposing of hydroxycholesta-5,7-diene to ultraviolet irradiation is conducted until the conversion of the hydroxycholesta-5,7-diene reaches 0.1–50%.

9. A process for preparing an active-type vitamin $D_3$ compound of the following formula [IV]

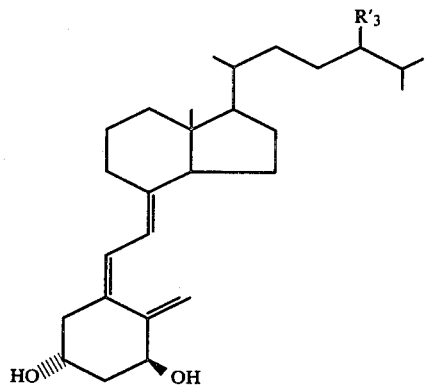

wherein R₃' represents a hydrogen atom or a hydroxyl group, which consists essentially of:

(i) exposing a hydroxycholesta-5,7-diene of the following formula [II]

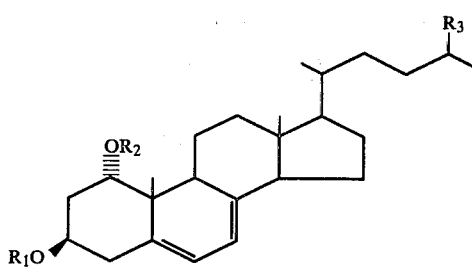

wherein $R_1$ and $R_2$ represent a lower alkoxycarbonyl group, $R_3$ represents a hydrogen atom or a lower alkoxycarbonyloxy group, to ultraviolet irradiation in an inert organic solvent to obtain a mixture of previtamin $D_3$ compounds of the following formula [III]

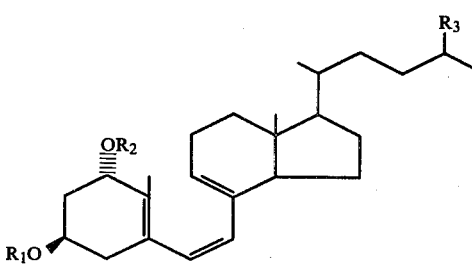

wherein $R_1$, $R_2$ and $R_3$ are the same as defined above, and the unchanged hydroxycholesta-5,7-diene of the formula [II];

(ii) separating the mixture by means of recrystallization or rinse into the previtamin $D_3$ compound and the unchanged hydroxycholesta-5,7-diene;

(iii) recycling the unchanged hydroxycholesta-5,7-diene through the ultraviolet irradiation; and (iv) thermally isomerizing the previtamin $D_3$ compound, and splitting off the protective groups.

10. The process of claim 9 wherein $R_1$ and $R_2$ in the hydroxycholesta-5,7-diene of the formula [II] are an ethoxycarbonyl or a methoxycarbonyl group.

11. The process of claim 9 wherein the exposing of the hydroxycholesta-5,7-diene to ultraviolet irradiation is conducted until the conversion of the hydroxycholesta-5,7-diene reaches 0.1–50%.

12. A process for preparing an active-type vitamin $D_3$ compound of the following formula [IV]

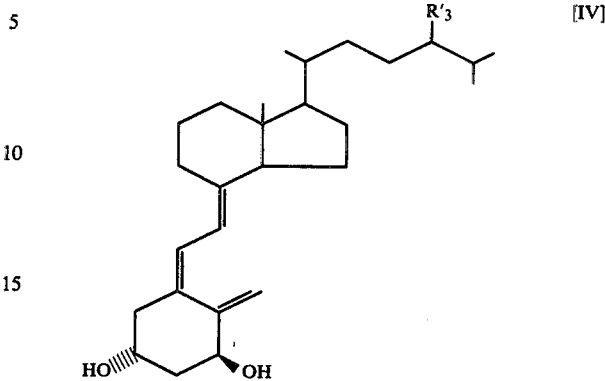

wherein R₃' represent a hydrogen atom or a hydroxyl group, which consists essentially of:

(i) exposing hydroxycholesta-5,7-diene of the following formula [II]

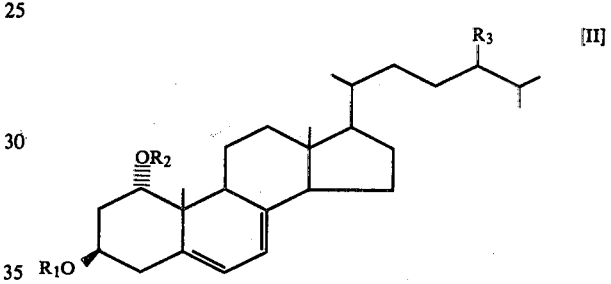

wherein $R_1$ and $R_2$ represent a lower alkoxycarbonyl group, $R_3$ represents a hydrogen atom or a lower alkoxycarbonyloxy group, to ultraviolet irradiation in an inert organic solvent, then thermally isomerizing to obtain a mixture of a protected active-type vitamin $D_3$ compound of the following formula [V]

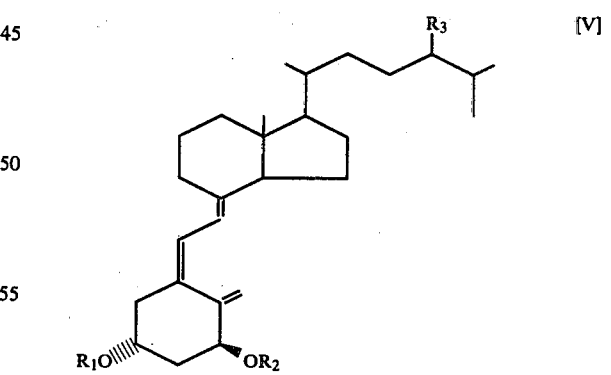

wherein $R_1$, $R_2$ and $R_3$ are the same as defined above, and the unchanged hydroxycholesta-5,7-diene of the formula [II];

(ii) separating the mixture by means of recrystallization or rinse into the protected active-type vitamin $D_3$ compound and the unchanged hydroxycholesta-5,7-diene;

(iii) recycling the unchanged hydroxycholesta-5,7-dienes through the ultraviolet irradiation; and (iv) splitting off the protective groups of the protected active-type vitamin $D_3$ compound.

13. The process of claim 12 wherein $R_1$ and $R_2$ in the hydroxycholesta-5,7-diene of the formula [II] are an ethoxycarbonyl or a methoxycarbonyl group.

14. The process of the claim 12 wherein the exposing of the hydroxycholesta-5,7-diene to the ultraviolet irradiation is conducted until the conversion of the hydroxycholesta-5,7-diene reaches 0.1–50%.

* * * * *